US010987165B2

(12) United States Patent
Rick et al.

(10) Patent No.: US 10,987,165 B2
(45) Date of Patent: *Apr. 27, 2021

(54) REFLECTIVE POWER MONITORING FOR MICROWAVE APPLICATIONS

(71) Applicant: COVIDIEN LP, Mansfield, MA (US)

(72) Inventors: Kyle R. Rick, Boulder, CO (US); Joseph A. Paulus, Lafayette, CO (US); Darion R. Peterson, Longmont, CO (US); Mani N. Prakash, Boulder, CO (US); Francesca Rossetto, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 351 days.

This patent is subject to a terminal disclaimer.

(21) Appl. No.: 15/823,868

(22) Filed: Nov. 28, 2017

(65) Prior Publication Data

US 2018/0078308 A1    Mar. 22, 2018

Related U.S. Application Data

(63) Continuation of application No. 14/691,080, filed on Apr. 20, 2015, now Pat. No. 9,827,043, which is a
(Continued)

(51) Int. Cl.
*A61B 18/18* (2006.01)
*A61B 17/00* (2006.01)
*A61B 18/00* (2006.01)

(52) U.S. Cl.
CPC .......... *A61B 18/1815* (2013.01); *A61B 18/18* (2013.01); *A61B 2017/00026* (2013.01);
(Continued)

(58) Field of Classification Search
CPC ............... A61B 18/18; A61B 18/1815; A61B 2018/00642; A61B 2018/00678;
(Continued)

(56) References Cited

U.S. PATENT DOCUMENTS 4,140,130 A     2/1979   Storm, III
4,311,154 A     1/1982   Sterzer et al.
(Continued)

FOREIGN PATENT DOCUMENTS

EP     0521264 A2    1/1993
EP     0667126 A1    8/1995
(Continued)

OTHER PUBLICATIONS

U.S. Pat. No. 5,326,343, Jul. 1994, Rudie et al. (withdrawn).
(Continued)

*Primary Examiner* — Ronald Hupczey, Jr.

(57) ABSTRACT

A system and method for supplying microwave energy to tissue for microwave therapy includes an electrosurgical generator having an output for coupling to a surgical instrument. The electrosurgical generator includes a microwave energy source and a controller for controlling the operation of the electrosurgical generator. The surgical instrument, coupled to the electrosurgical generator, includes a microwave antenna for delivering microwave energy from the microwave energy source. The controller of the electrosurgical generator is operable for causing the electrosurgical generator to apply at least two pulses of microwave energy.

17 Claims, 4 Drawing Sheets

Related U.S. Application Data continuation of application No. 11/820,679, filed on Jun. 20, 2007, now Pat. No. 9,023,024.

(52) U.S. Cl.
CPC ............... *A61B 2017/00044* (2013.01); *A61B 2017/00084* (2013.01); *A61B 2017/00154* (2013.01); *A61B 2018/00577* (2013.01); *A61B 2018/00642* (2013.01); *A61B 2018/00702* (2013.01); *A61B 2018/00726* (2013.01); *A61B 2018/00761* (2013.01); *A61B 2018/00785* (2013.01); *A61B 2018/00791* (2013.01); *A61B 2018/00839* (2013.01); *A61B 2018/00875* (2013.01)

(58) Field of Classification Search
CPC ........... A61B 2018/00702; A61B 2018/00708; A61B 2018/00726; A61B 2018/00732; A61B 2018/00761; A61B 2018/00785; A61B 2018/00797; A61B 2018/1861
See application file for complete search history.

(56) References Cited

U.S. PATENT DOCUMENTS

| | | | |
|---|---|---|---|
| 4,409,993 A | 10/1983 | Furihata | |
| 4,534,347 A | 8/1985 | Taylor | |
| 4,557,272 A | 12/1985 | Carr | |
| 4,583,869 A | 4/1986 | Chive et al. | |
| 4,612,940 A | 9/1986 | Kasevich et al. | |
| 4,621,642 A | 11/1986 | Chen | |
| 4,658,836 A | 4/1987 | Turner | |
| 4,700,716 A | 10/1987 | Kasevich et al. | |
| 4,776,086 A | 10/1988 | Kasevich et al. | |
| 4,800,899 A | 1/1989 | Elliott | |
| 4,823,812 A | 4/1989 | Eshel et al. | |
| 4,841,988 A | 6/1989 | Fetter et al. | |
| 4,945,912 A | 8/1990 | Langberg | |
| 5,097,845 A | 3/1992 | Fetter et al. | |
| 5,122,137 A | 6/1992 | Lennox | |
| 5,190,054 A | 3/1993 | Fetter et al. | |
| 5,221,269 A | 6/1993 | Miller et al. | |
| 5,234,004 A | 8/1993 | Hascoet et al. | |
| 5,246,438 A | 9/1993 | Langberg | |
| 5,249,585 A | 10/1993 | Turner et al. | |
| 5,275,597 A * | 1/1994 | Higgins .................. | A61B 17/22 606/33 |
| 5,281,217 A | 1/1994 | Edwards et al. | |
| 5,301,687 A | 4/1994 | Wong et al. | |
| 5,314,466 A | 5/1994 | Stern et al. | |
| 5,342,355 A | 8/1994 | Long | |
| 5,344,441 A | 9/1994 | Gronauer | |
| 5,366,490 A | 11/1994 | Edwards et al. | |
| 5,370,644 A | 12/1994 | Langberg | |
| 5,383,922 A | 1/1995 | Zipes et al. | |
| 5,405,346 A | 4/1995 | Grundy et al. | |
| 5,413,588 A | 5/1995 | Rudie et al. | |
| 5,458,597 A | 10/1995 | Edwards et al. | |
| 5,464,445 A | 11/1995 | Rudie et al. | |
| 5,480,417 A | 1/1996 | Hascoet et al. | |
| 5,500,012 A | 3/1996 | Brucker et al. | |
| 5,507,743 A | 4/1996 | Edwards et al. | |
| 5,509,929 A | 4/1996 | Hascoet et al. | |
| 5,520,684 A | 5/1996 | Imran | |
| 5,536,267 A | 7/1996 | Edwards et al. | |
| 5,545,137 A | 8/1996 | Rudie et al. | |
| 5,556,377 A | 9/1996 | Rosen et al. | |
| 5,599,294 A | 2/1997 | Edwards et al. | |
| 5,599,295 A | 2/1997 | Rosen et al. | |
| 5,628,770 A | 5/1997 | Thome et al. | |
| 5,628,771 A * | 5/1997 | Mizukawa .............. | A61B 18/18 606/31 |
| 5,683,382 A | 11/1997 | Lenihan et al. | |
| 5,720,718 A | 2/1998 | Rosen et al. | |
| 5,741,249 A | 4/1998 | Moss et al. | |
| 5,755,754 A | 5/1998 | Rudie et al. | |
| 5,776,176 A | 7/1998 | Rudie | |
| 5,800,486 A | 9/1998 | Thome et al. | |
| 5,810,803 A | 9/1998 | Moss et al. | |
| 5,810,804 A | 9/1998 | Gough et al. | |
| 5,829,519 A | 11/1998 | Uthe | |
| 5,843,144 A | 12/1998 | Rudie et al. | |
| 5,871,523 A | 2/1999 | Fleischman et al. | |
| 5,897,554 A | 4/1999 | Chia et al. | |
| 5,902,251 A | 5/1999 | vanHooydonk | |
| 5,904,691 A | 5/1999 | Barnett et al. | |
| 5,904,709 A | 5/1999 | Arndt et al. | |
| 5,916,240 A | 6/1999 | Rudie et al. | |
| 5,916,241 A | 6/1999 | Rudie et al. | |
| 5,931,807 A | 8/1999 | McClure et al. | |
| 5,938,692 A | 8/1999 | Rudie | |
| 5,951,547 A | 9/1999 | Gough et al. | |
| 5,957,969 A | 9/1999 | Warner et al. | |
| 5,964,755 A | 10/1999 | Edwards | |
| 5,974,343 A | 10/1999 | Brevard et al. | |
| 5,980,563 A | 11/1999 | Tu et al. | |
| 5,997,532 A | 12/1999 | McLaughlin et al. | |
| 6,009,351 A * | 12/1999 | Flachman ........... | A61B 18/1815 607/101 |
| 6,016,811 A | 1/2000 | Knopp et al. | |
| 6,026,331 A | 2/2000 | Feldberg et al. | |
| 6,029,051 A | 2/2000 | Osterberg et al. | |
| 6,032,078 A | 2/2000 | Rudie | |
| 6,047,216 A | 4/2000 | Carl et al. | |
| 6,056,744 A | 5/2000 | Edwards | |
| 6,059,780 A | 5/2000 | Gough et al. | |
| 6,063,078 A | 5/2000 | Wittkampf | |
| 6,073,051 A | 6/2000 | Sharkey et al. | |
| 6,080,150 A | 6/2000 | Gough | |
| 6,097,985 A | 8/2000 | Kasevich et al. | |
| 6,106,518 A | 8/2000 | Wittenberger et al. | |
| 6,122,551 A | 9/2000 | Rudie et al. | |
| 6,134,476 A | 10/2000 | Arndt et al. | |
| 6,146,379 A | 11/2000 | Fleischman et al. | |
| 6,176,856 B1 | 1/2001 | Jandak et al. | |
| 6,181,970 B1 | 1/2001 | Kasevich | |
| 6,216,703 B1 * | 4/2001 | Manker .................. | A61B 18/18 128/898 |
| 6,217,528 B1 | 4/2001 | Koblish et al. | |
| 6,223,086 B1 | 4/2001 | Carl et al. | |
| 6,226,553 B1 | 5/2001 | Carl et al. | |
| 6,233,490 B1 | 5/2001 | Kasevich | |
| 6,235,048 B1 | 5/2001 | Dobak, III | |
| 6,245,064 B1 | 6/2001 | Lesh et al. | |
| 6,251,128 B1 | 6/2001 | Knopp et al. | |
| 6,275,738 B1 | 8/2001 | Kasevich et al. | |
| 6,277,113 B1 | 8/2001 | Berube | |
| 6,289,249 B1 | 9/2001 | Arndt et al. | |
| 6,290,715 B1 | 9/2001 | Sharkey et al. | |
| 6,306,132 B1 | 10/2001 | Moorman et al. | |
| 6,325,796 B1 | 12/2001 | Berube et al. | |
| 6,330,479 B1 | 12/2001 | Stauffer | |
| 6,346,104 B2 | 2/2002 | Daly et al. | |
| 6,347,251 B1 | 2/2002 | Deng | |
| 6,350,262 B1 | 2/2002 | Ashley | |
| 6,355,033 B1 | 3/2002 | Moorman et al. | |
| 6,383,182 B1 | 5/2002 | Berube et al. | |
| 6,405,733 B1 | 6/2002 | Fogarty et al. | |
| 6,471,696 B1 | 10/2002 | Berube et al. | |
| 6,496,737 B2 | 12/2002 | Rudie et al. | |
| 6,496,738 B2 | 12/2002 | Carr | |
| 6,506,189 B1 | 1/2003 | Rittman, III et al. | |
| 6,512,956 B2 | 1/2003 | Arndt et al. | |
| 6,514,251 B1 | 2/2003 | Ni et al. | |
| 6,530,922 B2 | 3/2003 | Cosman et al. | |
| 6,564,806 B1 | 5/2003 | Fogarty et al. | |
| 6,569,159 B1 | 5/2003 | Edwards et al. | |
| 6,589,234 B2 | 7/2003 | Lalonde et al. | |
| 6,592,579 B2 | 7/2003 | Arndt et al. | |
| 6,663,624 B2 | 12/2003 | Edwards et al. | |
| 6,675,050 B2 | 1/2004 | Arndt et al. | |
| 6,685,700 B2 | 2/2004 | Behl et al. | |
| 6,699,241 B2 | 3/2004 | Rappaport et al. | |

(56) References Cited

U.S. PATENT DOCUMENTS

| | | |
|---|---|---|
| 6,706,040 B2 | 3/2004 | Mahon et al. |
| 6,722,371 B1 | 4/2004 | Fogarty et al. |
| 6,752,154 B2 | 6/2004 | Fogarty et al. |
| 6,752,767 B2 | 6/2004 | Turovskiy et al. |
| 6,823,218 B2 | 11/2004 | Berube |
| 6,852,091 B2 | 2/2005 | Edwards et al. |
| 6,878,147 B2 | 4/2005 | Prakash et al. |
| 7,070,595 B2 | 7/2006 | Ormsby et al. |
| 7,128,739 B2 | 10/2006 | Prakash et al. |
| 7,147,632 B2 | 12/2006 | Prakash et al. |
| 7,174,217 B2 | 2/2007 | Rioux et al. |
| 7,190,989 B1 | 3/2007 | Swanson et al. |
| 7,207,985 B2 | 4/2007 | Duong et al. |
| 7,217,282 B2 | 5/2007 | Ginsburg et al. |
| 7,229,437 B2 | 6/2007 | Johnson et al. |
| 7,231,259 B2 | 6/2007 | Jenney et al. |
| 7,234,225 B2 | 6/2007 | Johnson et al. |
| 7,234,977 B2 | 6/2007 | Westlund et al. |
| 7,235,070 B2 | 6/2007 | Vanney |
| 7,238,166 B2 | 7/2007 | Callister |
| 7,238,184 B2 | 7/2007 | Megerman et al. |
| 7,238,194 B2 | 7/2007 | Monstadt et al. |
| 7,241,293 B2 | 7/2007 | Davison |
| 7,244,254 B2 | 7/2007 | Brace et al. |
| 7,245,955 B2 | 7/2007 | Rashidi |
| 7,264,619 B2 | 9/2007 | Venturelli |
| 7,270,656 B2 | 9/2007 | Gowda et al. |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,270,662 B2 | 9/2007 | Visram et al. |
| 7,271,363 B2 | 9/2007 | Lee et al. |
| 7,273,480 B2 | 9/2007 | Young et al. |
| 7,276,061 B2 | 10/2007 | Schaer et al. |
| 7,282,049 B2 | 10/2007 | Orszulak et al. |
| 7,285,116 B2 | 10/2007 | de la Rama et al. |
| 7,293,562 B2 | 11/2007 | Malecki et al. |
| 7,300,438 B2 | 11/2007 | Falwell et al. |
| 7,301,131 B2 | 11/2007 | Gauthier et al. |
| 7,306,592 B2 | 12/2007 | Morgan et al. |
| 7,309,325 B2 | 12/2007 | Mulier et al. |
| 7,309,336 B2 | 12/2007 | Ashley et al. |
| 7,311,702 B2 | 12/2007 | Tallarida et al. |
| 7,311,703 B2 | 12/2007 | Turovskiy et al. |
| 7,311,705 B2 | 12/2007 | Sra |
| 7,317,949 B2 | 1/2008 | Morrison et al. |
| 7,318,822 B2 | 1/2008 | Darmos et al. |
| 7,318,823 B2 | 1/2008 | Sharps et al. |
| 7,318,824 B2 | 1/2008 | Prakash et al. |
| 7,319,904 B2 | 1/2008 | Cross, Jr. et al. |
| 7,326,204 B2 | 2/2008 | Paul et al. |
| 7,326,205 B2 | 2/2008 | Paul et al. |
| 7,326,206 B2 | 2/2008 | Paul et al. |
| 7,331,957 B2 | 2/2008 | Woloszko et al. |
| 7,337,009 B2 | 2/2008 | Schell |
| 7,553,309 B2 * | 6/2009 | Buysse ............... A61B 18/1206 606/34 |
| 9,023,024 B2 * | 5/2015 | Rick ....................... A61B 18/18 606/33 |
| 9,827,043 B2 * | 11/2017 | Rick ....................... A61B 18/18 |
| 2001/0001819 A1 | 5/2001 | Lee et al. |
| 2001/0008966 A1 | 7/2001 | Arndt et al. |
| 2001/0020178 A1 | 9/2001 | Arndt et al. |
| 2001/0020180 A1 | 9/2001 | Arndt et al. |
| 2001/0037812 A1 | 11/2001 | Dobak et al. |
| 2002/0022832 A1 | 2/2002 | Mikus et al. |
| 2002/0087151 A1 | 7/2002 | Mody et al. |
| 2002/0133148 A1 | 9/2002 | Daniel et al. |
| 2002/0147444 A1 | 10/2002 | Shah et al. |
| 2002/0198520 A1 | 12/2002 | Coen et al. |
| 2003/0004506 A1 | 1/2003 | Messing |
| 2003/0065317 A1 | 4/2003 | Rudie et al. |
| 2003/0069578 A1 | 4/2003 | Hall et al. |
| 2003/0078573 A1 | 4/2003 | Truckai et al. |
| 2003/0088242 A1 | 5/2003 | Prakash et al. |
| 2003/0109862 A1 | 6/2003 | Prakash et al. |
| 2003/0195499 A1 | 10/2003 | Prakash et al. |
| 2004/0078038 A1 | 4/2004 | Desinger et al. |
| 2004/0167517 A1 | 8/2004 | Desinger et al. |
| 2004/0168692 A1 | 9/2004 | Fogarty et al. |
| 2004/0243200 A1 | 12/2004 | Turner et al. |
| 2004/0267156 A1 | 12/2004 | Turovskiy et al. |
| 2005/0015081 A1 | 1/2005 | Turovskiy et al. |
| 2005/0065508 A1 | 3/2005 | Johnson et al. |
| 2005/0085881 A1 | 4/2005 | Prakash et al. |
| 2005/0107783 A1 | 5/2005 | Tom et al. |
| 2005/0148836 A1 | 7/2005 | Kleen et al. |
| 2005/0159741 A1 | 7/2005 | Paul et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2006/0287649 A1 | 12/2006 | Ormsby et al. |
| 2007/0027451 A1 | 2/2007 | Desinger et al. |
| 2007/0073282 A1 | 3/2007 | McGaffigan et al. |
| 2007/0123765 A1 | 5/2007 | Hetke et al. |
| 2007/0129715 A1 | 6/2007 | Eggers et al. |
| 2007/0135879 A1 | 6/2007 | McIntyre et al. |
| 2007/0142829 A1 | 6/2007 | Ahn et al. |
| 2007/0149964 A1 | 6/2007 | Kawabata et al. |
| 2007/0156048 A1 | 7/2007 | Panescu et al. |
| 2007/0156128 A1 | 7/2007 | Jimenez |
| 2007/0156132 A1 | 7/2007 | Drysen |
| 2007/0156133 A1 | 7/2007 | McDaniel et al. |
| 2007/0173680 A1 | 7/2007 | Rioux et al. |
| 2007/0173798 A1 | 7/2007 | Adams et al. |
| 2007/0173812 A1 | 7/2007 | Bonan et al. |
| 2007/0179375 A1 | 8/2007 | Fuimaono et al. |
| 2007/0179497 A1 | 8/2007 | Eggers et al. |
| 2007/0185478 A1 | 8/2007 | Cosentino |
| 2007/0191825 A1 | 8/2007 | Cronin et al. |
| 2007/0203551 A1 | 8/2007 | Cronin et al. |
| 2007/0208334 A1 | 9/2007 | Woloszko et al. |
| 2007/0208335 A1 | 9/2007 | Woloszko et al. |
| 2007/0208383 A1 | 9/2007 | Williams |
| 2007/0213700 A1 | 9/2007 | Davison et al. |
| 2007/0213703 A1 | 9/2007 | Naam et al. |
| 2007/0215163 A1 | 9/2007 | Harrington et al. |
| 2007/0219551 A1 | 9/2007 | Honour et al. |
| 2007/0225701 A1 | 9/2007 | O'Sullivan |
| 2007/0233057 A1 | 10/2007 | Konishi |
| 2007/0244529 A1 | 10/2007 | Choi et al. |
| 2007/0250053 A1 | 10/2007 | Fernald et al. |
| 2007/0250054 A1 | 10/2007 | Drake |
| 2007/0250055 A1 | 10/2007 | Johnson et al. |
| 2007/0250056 A1 | 10/2007 | Vanney |
| 2007/0255276 A1 | 11/2007 | Sliwa et al. |
| 2007/0260235 A1 | 11/2007 | Podhajsky |
| 2007/0260237 A1 | 11/2007 | Sutton et al. |
| 2007/0270679 A1 | 11/2007 | Nguyen et al. |
| 2007/0270791 A1 | 11/2007 | Wang et al. |
| 2007/0276361 A1 | 11/2007 | Stevens-Wright et al. |
| 2007/0276362 A1 | 11/2007 | Rioux et al. |
| 2007/0282323 A1 | 12/2007 | Woloszko et al. |
| 2007/0282324 A1 | 12/2007 | Vaska et al. |
| 2007/0282325 A1 | 12/2007 | Young et al. |
| 2007/0287995 A1 | 12/2007 | Mayse |
| 2007/0287998 A1 | 12/2007 | Sharareh et al. |
| 2007/0293853 A1 | 12/2007 | Truckai et al. |
| 2007/0293854 A1 | 12/2007 | Pless et al. |
| 2007/0293855 A1 | 12/2007 | Sliwa et al. |
| 2007/0299488 A1 | 12/2007 | Carr |
| 2008/0004614 A1 | 1/2008 | Burdette et al. |
| 2008/0004618 A1 | 1/2008 | Johnson et al. |

FOREIGN PATENT DOCUMENTS

| | | |
|---|---|---|
| EP | 1810627 A1 | 7/2007 |
| JP | 200137775 A | 2/2001 |
| WO | 9320767 A1 | 10/1993 |
| WO | 9320768 A1 | 10/1993 |
| WO | 9634571 A1 | 11/1996 |
| WO | 9748449 A1 | 12/1997 |
| WO | 9748450 A1 | 12/1997 |
| WO | 9748451 A1 | 12/1997 |

(56) References Cited

FOREIGN PATENT DOCUMENTS

| WO | 9956642 A1 | 11/1999 |
|---|---|---|
| WO | 9956643 A1 | 11/1999 |
| WO | 9956812 A2 | 11/1999 |
| WO | 0049957 A1 | 8/2000 |
| WO | 0051513 A1 | 9/2000 |
| WO | 0057811 A1 | 10/2000 |
| WO | 01060235 A2 | 8/2001 |
| WO | 0278777 A1 | 10/2002 |
| WO | 03034932 A1 | 5/2003 |
| WO | 03039385 A2 | 5/2003 |
| WO | 2003/047043 A1 | 6/2003 |
| WO | 2003/088806 A2 | 10/2003 |
| WO | 2003/088858 | 10/2003 |
| WO | 2005011049 A2 | 2/2005 |
| WO | 2005016119 A2 | 2/2005 |

OTHER PUBLICATIONS

I Chou, C.K., "Radiofrequency Hyperthermia in Cancer Therapy," Biologic Effects of Nonionizing Electromagnetic Fields, Chapter 94, CRC Press, Inc., (1995), pp. 1424-1428.
International Search Report—EP 06 00 9435 dated Jul. 13, 2006.
Japanese Official Action and Preliminary Report from Appl. No. JP 2008-161057 dated Dec. 14, 2012.
Canadian Office Action from Appl. No. 2,635,389 dated Feb. 17, 2017.

* cited by examiner

REFLECTIVE POWER MONITORING FOR MICROWAVE APPLICATIONS

CROSS-REFERENCE TO RELATED APPLICATIONS

This application is a continuation application of U.S. patent application Ser. No. 14/691,080, filed Apr. 20, 2015, now U.S. Pat. No. 9,827,043, which is a continuation application of U.S. patent application Ser. No. 11/820,679, filed Jun. 20, 2007, now U.S. Pat. No. 9,023,024, the entire contents of which are incorporated herein by reference.

BACKGROUND

Technical Field

The present disclosure relates generally to medical/surgical ablation procedures. More particularly, the present disclosure relates to devices and microwave radiation delivery procedures utilizing microwave antenna assemblies and methods of controlling the delivery of microwave radiation to tissue.

Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Additionally, microwave therapy may be used in the treatment of tissue and organs such as the prostate, heart, and liver.

One advantage of microwave therapy is that microwave energy is able to non-invasively penetrate the skin to reach underlying tissue. Unlike low frequency RF therapy, which heats tissue with current, microwave therapy heats tissue within the electromagnetic field generated by a microwave antenna. The electromagnetic field generated by the microwave antenna generates a predictably large and/or uniformed ablation region.

A second advantage of microwave therapy is that energy is rapidly delivered to the target tissue resulting in the reduction of surgical procedure time. During a typical surgical procedure microwave energy rapidly heats tissue to a target temperature and maintains the tissue above the target temperature for a required period of time.

Rapid delivery of heat to tissue may also result in the unwanted heating of healthy tissue or overheating of the target tissue. Unwanted heating of healthy tissue may be the result of creating an electromagnetic field larger than is required or excessive energy delivery. Overheating of tissue may result from excessive energy delivery or inconsistent heating of the target tissue.

Thus, the non-invasive use of microwave energy requires a great deal of control. This is partly why a more direct and precise method of delivering microwave radiation has been sought. The present disclosure provides a system for supplying microwave and various methods of delivering microwave radiation to tissue.

SUMMARY

The present disclosure relates generally medical/surgical ablation procedures. More particularly, the present disclosure relates to monitoring characteristics of microwave radiation delivery procedures utilizing microwave antenna assemblies configured for direct insertion into tissue and methods of controlling the delivery of microwave radiation to tissue.

A system for supplying microwave energy for microwave therapy of the present disclosure comprises an electrosurgical generator including a microwave energy source and a controller for controlling the operation of an electrosurgical generator. The electrosurgical generator includes an output for coupling to a surgical instrument which includes a microwave antenna for delivering microwave energy. The controller being operable for causing the electrosurgical generator to apply two or more pulses of microwave energy to the tissue.

The controller may be configured to measure an electrical characteristic of at least one of the at least two pulses of microwave energy. Controller may be responsive to the measured electrical characteristic of at least one of the at least two pulses of microwave energy for determining at least one pulse parameter of a subsequent microwave energy pulse. The pulse parameter may be selected from a group consisting of power, frequency, pulse duration, pulse duty cycle and time between pulses. The electrical characteristic may be related to reflective power. The controller may vary the power of each of the pulses of microwave energy. Controller may also be responsive to a control input from an operator for modifying any one of the at least one pulse parameters.

A method for applying microwave energy to target tissues includes the steps of positioning the microwave energy delivery device into or adjacent a portion of the target tissue and delivering at least two pulses of microwave energy to the target tissue wherein a substantial portion of the microwave energy is reduced between the at least two pulses of microwave energy. The delivering step may include the steps of heating a portion of the target tissue to a target temperature and maintaining the portion of the target tissue at or above the target temperature In another embodiment the step of delivering the at least two pulses of microwave energy may include the step of selecting and varying at least one parameter thereof. The step of selecting and varying the at least one parameter may further include the step of selecting the at least one parameter from a group consisting of power, frequency, pulse duration, pulse duty cycle and time between pulses In yet another embodiment the step of delivering the at least two pulses of microwave energy may include the step of varying at least one of the at least two pulses of microwave energy in accordance with at least one characteristic of an electrical transient of one of the at least two pulses of microwave energy.

In yet another embodiment the step of delivering the at least two pulses of microwave energy may include the step of selecting parameters of the at least two pulses of microwave energy such that a rise in target tissue temperature is about zero.

In yet another embodiment the step of delivering the at least two pulses of microwave energy may include the steps of measuring at least one characteristic of the target tissue in response to one of the at least two pulses of microwave energy and in accordance with the at least one characteristic of the target tissue, determining whether to change the microwave energy parameters. The step of measuring the at least one characteristic of tissue may further include the step of selecting the at least one characteristic of the tissue from a group consisting of a characteristic related to reflective power, a characteristic related to tissue temperature, and a characteristic related to tissue impedance. The method may further include the step of determining a response of the target tissue to one of the at least two pulses of microwave energy.

In yet another embodiment the step of delivering the at least two pulses of microwave energy may include the steps of measuring at least one characteristic of one of the at least two pulses of microwave energy and in accordance with the at least one measured characteristic, determining whether to change at least one microwave energy parameter. The step of measuring the at least one characteristic of one of the at least two pulses of microwave energy may include the step of selecting at least one characteristic related to reflective power. The method may further include the steps of measuring at least one characteristic of one of the at least two pulses of microwave energy and in accordance with the at least one measured characteristic, at least one of determining whether to terminate the application of microwave energy to tissue, and using the at least one measured characteristic to determine a set of microwave energy parameters for a subsequent pulse of microwave energy. The at least one microwave energy parameter may be selected from a group consisting of power, frequency, pulse duration, pulse duty cycle and time between pulses.

In yet another embodiment the method of positioning the microwave energy delivery device into or adjacent a portion of the target tissue and delivering at least two pulses of microwave energy may include the steps of measuring at least one characteristic of the target tissue in response to one of the at least two pulses of microwave energy; and in accordance with the at least one characteristic of the target tissue, at least one of determining whether to terminate the application of microwave energy, and using the at least one characteristic of the target tissue to determine a set of microwave energy parameters for applying a subsequent pulse of microwave energy. The set of microwave energy parameters for the application of a subsequent pulse of microwave energy may includes a magnitude of a microwave power and a pulse duration of a subsequent pulse of microwave energy.

The delivery of microwave energy may be terminated upon a determination that a predetermined condition is satisfied. The predetermined condition is selected from a group consisting of treatment duration, a condition related to temperature and a condition related to reflective power.

In yet another embodiment of the present disclosure a method for applying microwave energy to a target tissue, includes the steps of positioning a microwave energy delivery device into or adjacent a portion of the target tissue, delivering at least two pulses of microwave energy to the target tissue wherein a substantial portion of the microwave energy is reduced between the at least two pulses of microwave energy, measuring at least one of the temperature of a transmission line and a temperature of the microwave energy delivery device, and varying at least one of the at least two pulses of microwave energy in response to the at least one of the measured temperatures.

DETAILED DESCRIPTION

Embodiments of the presently disclosed microwave antenna assembly will now be described in detail with reference to the drawing figures wherein like reference numerals identify similar or identical elements. As used herein and as is traditional, the term "distal" refers to the portion of the device or instrument that is furthest from the user and the term "proximal" refers to the portion of the device or instrument that is closest to the user. In addition, terms such as "above", "below", "forward", "rearward", etc. refer to the orientation of the figures or the direction of components and are simply used for convenience of description.

Two factors in the treatment of diseased tissue with microwave therapy include the proper positioning and placement of a microwave antenna relative to the target tissue, and the delivery of microwave energy.

The step of positioning and placement of a microwave antenna, relative to target tissue, is dependant upon the location of the target tissue. One method of accessing target tissue involves the insertion of the microwave antenna into an existing body lumen, such as, for example, accessing the inner chambers of the heart through the vascular system, accessing the prostate by inserting a microwave antenna through the urethra or accessing the lungs and esophagus by inserting a microwave antenna through the mouth cavity. Various methods and devices are provided for in U.S. Pat. No. 5,916,241, entitled "Device and Method for Asymmetrical Thermal Therapy with Helical Dipole Microwave Antenna", to Rudie et al., describing accessing the prostate through the urethra, and U.S. Pat. No. 7,070,595, entitled "Radio-Frequency Based Catheter System and Method for Ablating Biological Tissue", to Ormsby et al., describing accessing cardiac tissue through the vascular system.

Another method of accessing target tissue involves direct insertion of a device into tissue. A microwave antenna may be formed or inserted through a delivery device such as, for example, an introducer or catheter, as described in U.S. Pat. No. 6,355,033, entitled "Track Ablation Devices and Methods", to Moorman et al. The microwave antenna may also be sufficiently strong to allow direct insertion into tissue as described in U.S. Pat. No. 6,878,147, entitled "High Strength Microwave Antenna Assemblies", to Prakash et al. Yet another microwave device may be inserted into tissue in a first condition followed by deployment of the distal penetrating portion thereof to a second condition thereby forming a microwave antenna at the distal end of the assembly as described in U.S. application Ser. No. 10/272,314, entitled "Microwave Antenna Having a Curved Configuration", to Prakash et al.

The delivery of microwave energy is also dependant upon the location of the target tissue. Ormsby et al. '595 describes delivery of RF energy in the vascular system that generates and delivers a continuous train of radio frequency energy pulses at an output frequency for transmission in a transmission line to a shapeable RF antenna. The output frequency is adjusted based on the sensed reflective signal in order to substantially match the transmission line impedance with the shapeable RF antenna and the biological tissue load impedance. Rudie et al. '241 describes delivery of a continuous train of microwave energy in the urological system. In both Ormsby et al. '595 and Rudie et al. '241 the output frequency is adjusted to reduce the risk of overheating by the electrical transmission and to prevent damage to the lumen in which the transmission line is contained.

The present disclosure provides a system for supplying microwave energy and various methods of delivering microwave radiation to tissue with a microwave device. A microwave device of the system for supplying microwave energy may be inserted directly into tissue, inserted through a lumen, such as, for example, a vein, needle or catheter, placed into the body during surgery by a clinician or positioned in the body by other suitable methods or means known in the art. While the method described hereinbelow is targeted toward microwave ablation and the complete destruction of target tissue, the methods may be used with other microwave therapies in which the target tissue is partially damaged, e.g. in order to prevent the electrical conduction in heart tissue.

Figure 1:
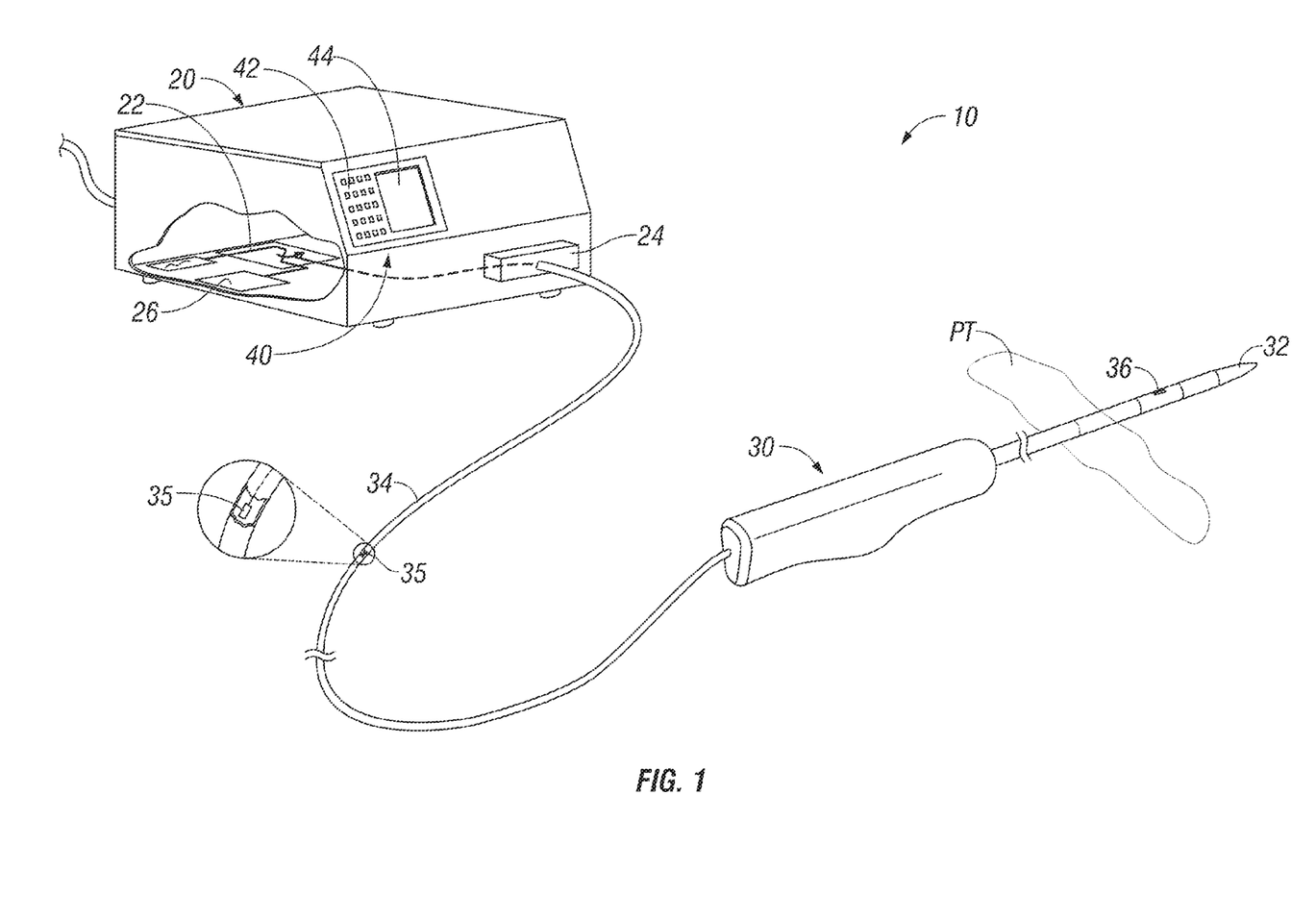
FIG. 1 is a schematic illustration of a system for supplying microwave energy for microwave therapy, according to an embodiment of the present disclosure.

Referring now to FIG. 1, a system for supplying microwave energy for microwave therapy, according to an embodiment of the present disclosure, is shown as 10. The system for supplying microwave energy 10 includes an electrosurgical generator 20, with a controller 22 for controlling the operation of the electrosurgical generator 20, an electrosurgical instrument or device 30 coupled to an output 24 on the electrosurgical generator 20. Device 30 includes a microwave antenna 32, for delivery of microwave energy, coupled to a transmission line 34, which electrically connects antenna 32 to output 24 on electrosurgical generator 20. Electrosurgical generator 20 includes an operator interface 40 having a keypad 42 and a display 44 for entering microwave energy parameters by an operator.

Device 30 is illustrated as a microwave antenna sufficiently strong to allow direct insertion or penetration into tissue, although microwave antenna may be any device suitably capable of delivering microwave energy or the like.

System 10 may include one or more sensors to measure various parameters associated with the delivery of microwave energy. For example, device 30 and/or transmission line 34 may include one or more suitable temperature measuring sensor 35, 36. As seen in FIG. 1, a first sensor 35 is connected to transmission line 34 and a second sensor 36 is connected to antenna 32. Sensors 35, 36 may connect to electrosurgical generator 20 through transmission line 34 and connector 24. Alternatively, a temperature sensor may be an independent device that connects directly to electrosurgical generator 20.

Figure 2:
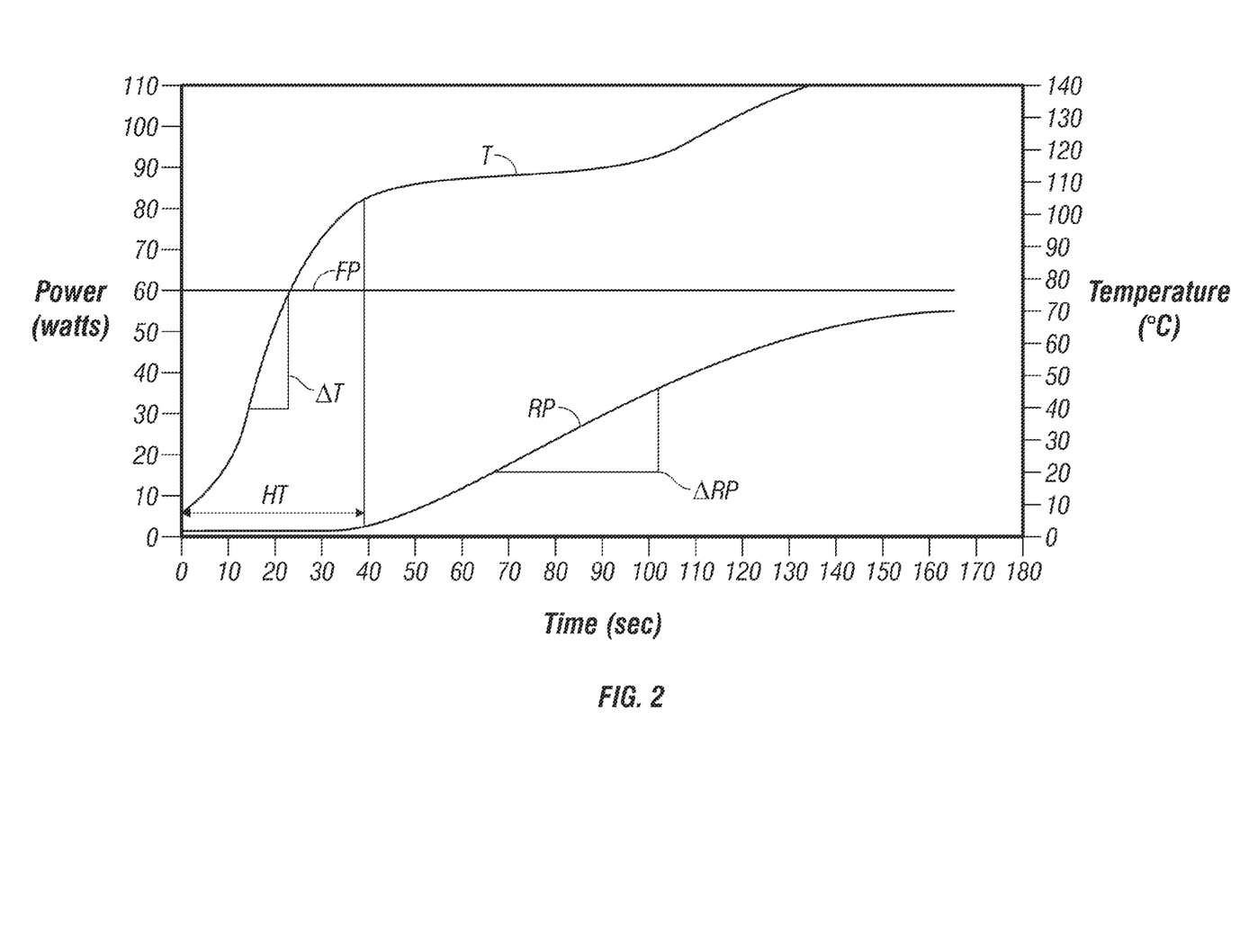
FIG. 2 illustrates various waveforms associated with electrical characteristics of microwave therapy performed with the system for supplying microwave energy of FIG. 1.

FIG. 2 illustrates various waveforms associated with electrical characteristics of microwave therapy performed with the system 10 of FIG. 1. A first waveform is forward power "FP" or power supplied to the antenna 32 by the electrosurgical generator 20. A second waveform is tissue temperature "T" measured by a temperature measuring sensor 36. A third waveform is reflected power "RF" or power that is not transmitted by the antenna 32 to tissue. Each waveform is related to the delivery of microwave energy.

During operation of system 10, as seen in FIG. 2, during an initial 40 seconds of operation, the temperature "T" of tissue begins to rise as energy is delivered to the tissue. Between 40 and 50 seconds of operation, the tissue temperature "T" exceeds 100° C. and the water or liquid in the patient tissue "PT" (see FIG. 1) begins to boil. Between 40 and 90 seconds of operation, tissue temperature "T" is maintained at a temperature slightly over 100° C. Between 90 and 100 seconds of operation, the water or liquid in the patient tissue "PT" is boiled off and the tissue temperature "T" again begins to rise. The energy supplied to patient tissue "PT", from system 10, begins to char the tissue "PT" and potentially irreversible changes or effects result in the tissue "PT".

FIG. 2 is provided as an example of waveforms associated with electrical characteristics of microwave therapy and should not be construed as limiting hereto. The systems and methods described herein may utilize other suitable waveforms associated with microwave therapy. The shape of the waveforms are dependant upon many factors (e.g., the type of tissue receiving the energy, the desired therapeutic result, the size and type of microwave antenna used and/or the power and frequency of the microwave energy.) For example, tissue with high fluid content, such as, for example, kidney tissue, liver tissue or cardiovascular tissue, may require more energy and time to heat than tissue with low fluid content, such as, for example, lung tissue.

The desired therapeutic result may also impact the shape of the individual waveforms. For example, during tissue ablation tissue temperature may rise to about 60° C. to 70° C. and the clinician may maintain the tissue at a temperature for a target amount of time. Other treatments may require raising tissue to a temperature less than 60° C. or may not require maintaining the tissue at a target temperature.

With continued reference to FIG. 2, electrosurgical generator 20 maintains forward power "FP" at approximately 60 Watts for the duration of the delivery of microwave energy.

During the initial delivery of microwave energy to patient tissue "PT", between 0 and 70 seconds, the antenna 32 is matched to the tissue properties and reflective power "RP" is at a minimum at a level slightly more than zero. Between 90 and 100 seconds the properties of patient tissue "PT" begin to change and reflective power "RP" begins to increase. This increase in reflective power "RP" indicates that the antenna 32 is less "tuned", or matched to the properties of tissue "PT", and less power is delivered to tissue "PT". At this point, electrosurgical generator 20 continues to maintain constant forward power "FP" and the antenna 32 become less efficient and reflective power continues to increase.

Reflective power may be reduced by adjusting the frequency of the delivered microwave energy to match the impedance of the damaged tissue. The present disclosure provides for a system and method of controlling the delivery of microwave energy in order to prevent and/or minimize a change in tissue impedance, thus preventing further increases in reflective power.

With reference to FIGS. 1 and 2, forward power "FP", temperature "T" and reflective power "RF" are waveforms, or electrical transients, related to microwave energy delivery. Controller 22 may be responsive to at least one characteristic of an electrical transient that occurs during at least one individual pulse of microwave energy. The characteristic of an electrical transient, or property of a given waveform, may include the rate of change of reflective power "ΔRF", rate of change of temperature "ΔT", rate of change of impedance (not shown) or rate of change of forward power "ΔFP". The transient may also be related to a particular phenomenon that occurs in the waveform, such as, for example, the heating time "HT" of tissue in response to the delivery of microwave power or the reaction time of tissue temperature in response to the removal of the delivery and/or transmission of microwave energy.

Controller 22 may also be responsive to an individual measurement related to microwave energy delivery, such as, for example, an instantaneous or time weighted measurement of temperature, power or impedance.

Figure 3:
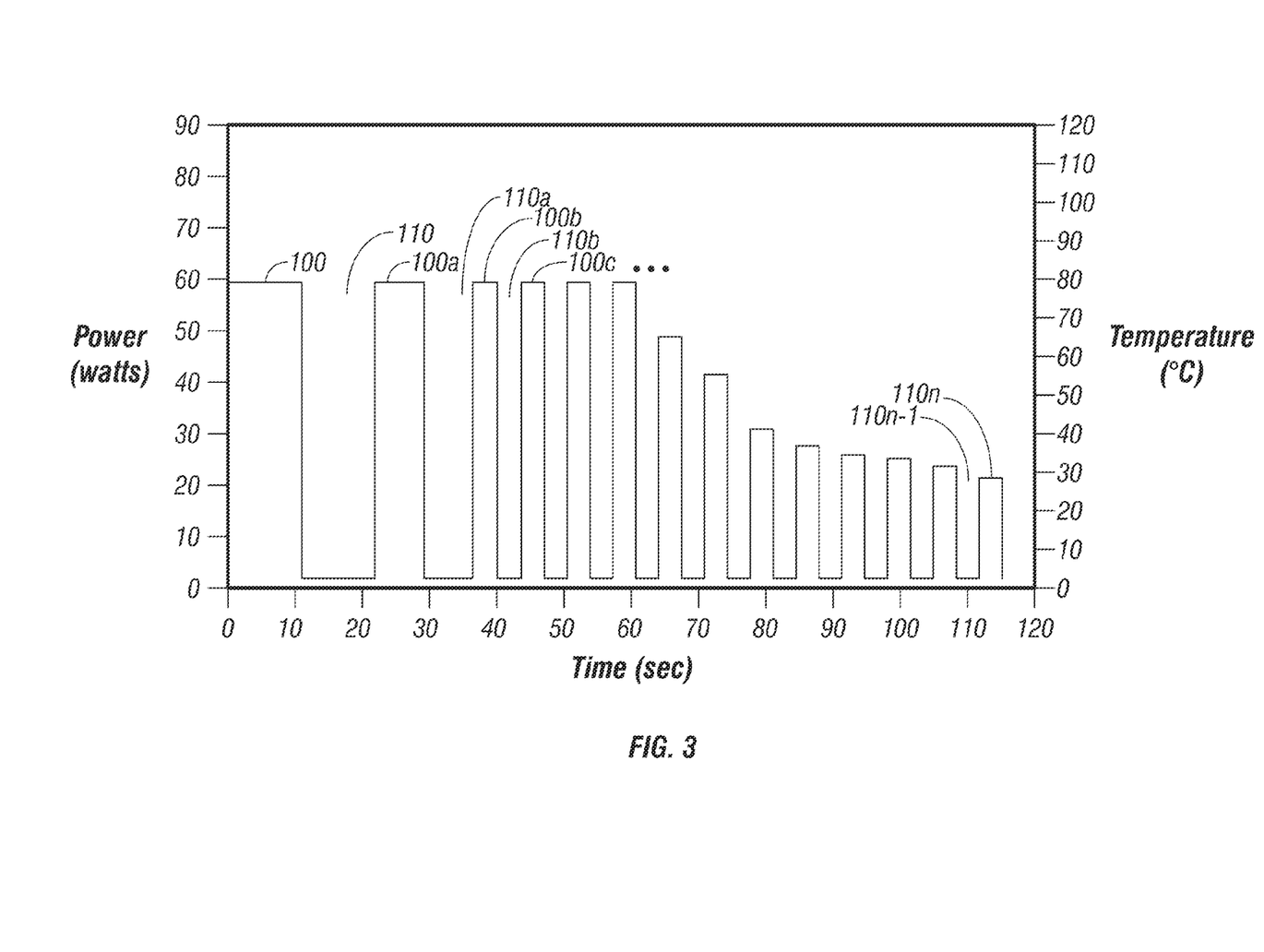
FIG. 3 illustrates microwave pulses generated by the system for supplying microwave energy of FIG. 1 according to a method of the present disclosure.

With reference to FIGS. 1 and 3, controller 22 is operable to cause the electrosurgical generator 20 to apply two or more pulses 100-100n of microwave energy to tissue. Each pulse of microwave energy is defined by various parameters such as, for example, frequency of the microwave energy, amount of power delivered by the microwave energy and the time duration of the microwave energy pulse.

Controller 22 is operable to remove, reduce or turn off the delivery of energy 110-110n to patient tissue "PT" between energy pulses 100-100n. With reference to FIG. 1, removal of energy delivery to patient tissue "PT" may be accomplished by switching the delivery of energy from the output 24 to a secondary load 26. Energy may be reduced by automatically adjusting, or by substantially reducing, the power delivered to the output 24. Alternatively, controller may turn off the energy delivered to the output 24.

The energy pulse generated by the controller, irrespective of the method of generation, is characterized by delivery of energy to tissue for an amount of time followed by a second amount of time wherein the energy delivered to tissue is substantially reduced. Preferably, the energy delivered to tissue during the second amount of time is reduced to a level that is metabolically insignificant, or equal to the basal metabolism level of about 1 W/kg of tissue.

The controller 22 may include means for switching (not explicitly shown) the delivery of energy to secondary load 26. The means for switching may be a separate device included in the electrosurgical generator 20 or it may be an external device controlled by the electrosurgical generator 20.

With continued reference to FIG. 1, controller 22 measures an electrical characteristic of the microwave energy delivered to patient tissue "PT" and is capable of adjusting one or more pulse parameters based on the measured electrical characteristic. Measurements may be made or performed by the electrosurgical generator 20, the controller 22, a sensor 36 in the device 30, a sensor 35 in transmission cable 34 or by a separate sensor (not explicitly shown) coupled to the electrosurgical generator 20. Controller 22 may vary the pulse parameter of the current microwave energy pulse or may vary the pulse parameter of any subsequent energy pulse. Controller 22 may also utilize the measured electrical characteristics of microwave energy to determine if the energy delivery should continue or if energy delivery should be terminated.

FIG. 3 illustrates at least one embodiment of microwave energy delivered to patient tissue "PT" by the system 10 of the present disclosure. The microwave energy is defined by a series of energy pulses 100 to 100n separated by delays 110-110n during which delays 110-110n the energy delivered to tissue "PT" is removed or is substantially reduced. First microwave pulse 100 is followed by a first delay 110, followed by one or more subsequent energy pulses 100a-n each of which is separated by a delay 110a-110n-1.

Providing microwave energy as a series of pulses, separated by delays, wherein the energy is removed or substantially reduced, improves delivery and dispersion of heat within the target tissue. Removing power provides a relaxation period for the tissue "PT" and enables the tissue "PT" to re-hydrate and recover. Microwave energy is then reapplied to tissue "PT" after the delay or relaxation period and the process may be repeated as needed and/or desired. This periodic redistribution of heat through the tissue "PT" during the relaxation period, followed by the re-delivery and/or re-transmission of microwave energy, improves the ablation size and results in a more predictable ablation area.

Microwave energy therapy parameters are used to determine the number of microwave energy pulses, the duration and power of each individual energy pulse, the delay between energy pulses and the total duration of the procedure. Individual pulse parameters include the parameters associated with each individual pulse, such as, for example, the duration of the pulse, the frequency of the pulse, the power setting of the pulse and the delay after each individual pulse. With reference to FIG. 1, parameters may be predetermined by a clinician and entered through the operator interface 40, may be determined by the controller 22 or may be entered through the keypad 42 by the clinician and adjusted by controller 22. Pulse parameters may be adjusted for each individual pulse. Alternatively, some parameters, such as the frequency of the microwave energy, may be consistent throughout the duration of the microwave energy therapy.

Controller 22 may be responsive to the measured electrical characteristics of one or more microwave energy pulses. The measured electrical characteristic may be related to reflective power, such as, for example, forward reflective power, reverse reflective power, reflection loss, reflection coefficient, voltage standing wave ratio (VSWR), return loss, or mismatch loss VSWR. The measured electrical characteristic may be a sensed parameter such as, for example, temperature of the transmission line 34 measured by sensor 35 or the temperature of the device 30 measured by device sensor 36. In operation, controller 22 may adjust one or more parameters of the current energy pulse or of a subsequent microwave energy pulse.

In the operation of one embodiment of the present disclosure, a clinician may view the various electrical characteristics related to reflective power, via the user interface 40 and display 44. The clinician may make adjustments to the microwave energy therapy parameters or pulse parameters based on the various electrical characteristics. The clinician may adjust one or more parameters of the current pulse or of a subsequent pulse or may adjust one or more microwave energy therapy parameters.

A first method of applying microwave therapy to tissue includes the steps of applying a first pulse of microwave energy to tissue, removing a substantial portion of the microwave energy from the tissue and applying at least one subsequent microwave energy pulse to tissue. Removing a substantial portion of the microwave energy may include: reducing the energy to a level that allows the tissue relaxes, reducing the energy to a level that maintains tissue temperature, reducing energy to a level that is metabolically insignificant, or reducing the delivered energy to zero.

As discussed hereinabove and with reference to FIG. 1, controller 22 may be responsive to at least one characteristic of an electrical transient that occurs during at least one individual pulse of microwave energy or may be responsive to a measurement related to microwave energy delivery. The step of applying at least one subsequent microwave energy pulse to tissue may include the step of selecting and varying at least one parameter for the subsequent microwave energy pulse. The parameter may be varied in accordance to an individual measurement or may be varied in accordance with at least one characteristic of an electrical transient that occurs during an individual pulse of microwave energy. The varied parameter may include, and is not limited to, forward power, frequency, energy pulse duration and termination of energy application.

Figure 4:
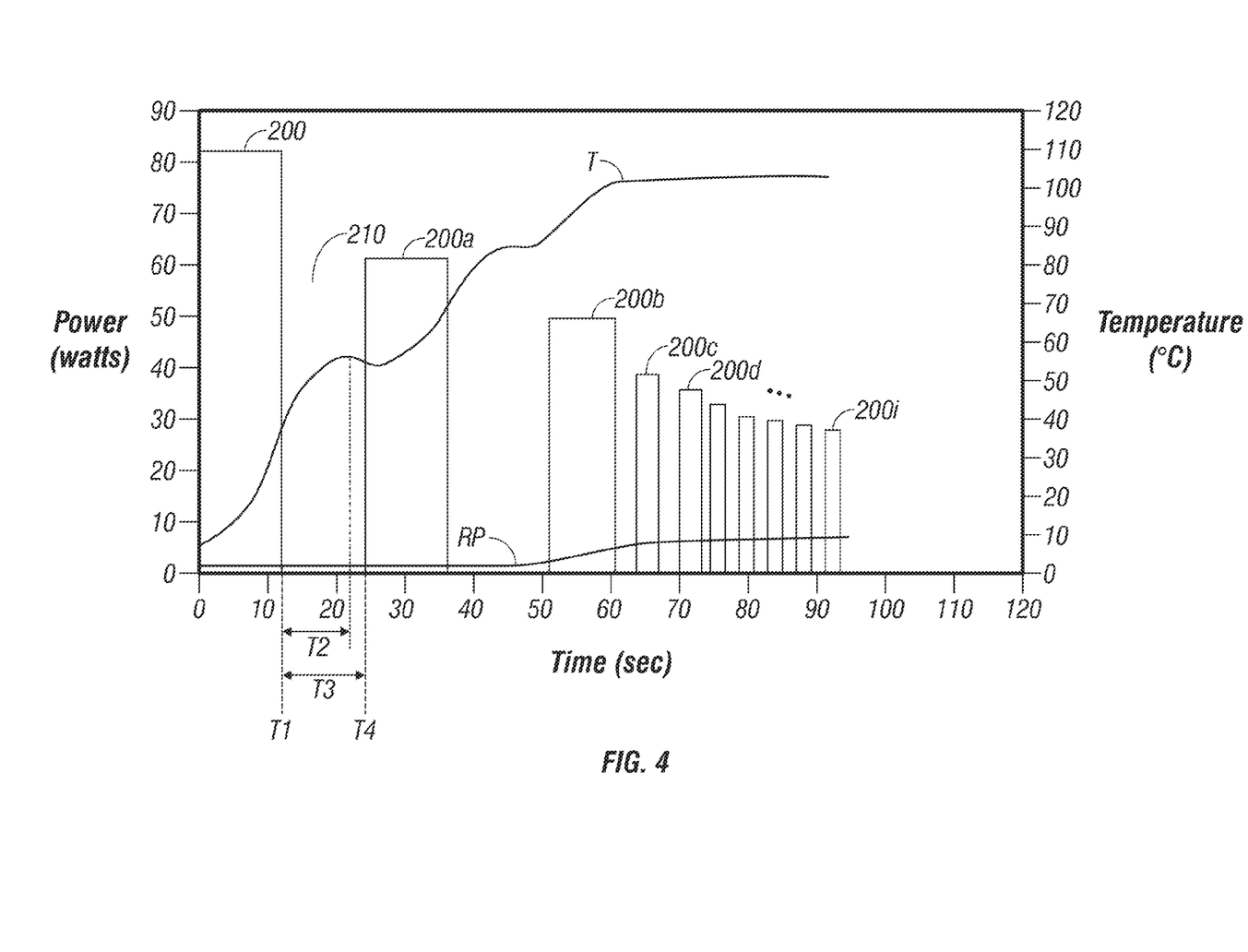
FIG. 4 illustrates microwave pulses generated by the system for supplying microwave energy of FIG. 1 according to another method of the present disclosure.

FIG. 4 provides an example of energy delivery in accordance with one embodiment of the present disclosure. With reference to FIGS. 1 and 4, initial energy pulse 200 is applied with a forward power setting of 80 watts. For the initial energy pulse 200, controller 22 may be responsive to a characteristic of tissue "PT", a characteristic of the microwave energy pulse and/or a characteristic of an electrical transient. Controller 22 terminates the initial energy pulse 200 when a rate of change of tissue temperature "T" exceeds a threshold value. The threshold value of the rate of change of tissue temperature may be a predetermined value, an operator entered value and/or a value calculated by controller 22. Alternatively, duration of the initial energy pulse 200 may be shortened or a pulse parameter, such as power, may be modified. In FIG. 4, the rate of change of temperature "T" terminates the initial energy pulse 200 at time "T1".

After the termination of the initial energy pulse 200, the temperature "T" may continue to rise for a period to time "T2" due to the heat dispersing within the target tissue. The duration of a first off period 210 having a period of time "T3" that may be equal to a predetermined amount of time. Controller 22 may vary the duration of the first off period 210 in response to a characteristic of tissue, a characteristic of a previous microwave energy pulse and/or a characteristic of an electrical transient. In FIG. 4, the first off period 210 terminates at time "T4" and the first subsequent energy pulse 200a is applied to the target tissue.

The individual pulse parameters of the first subsequent energy pulse 200a may be varied according to a characteristic of tissue, a characteristic of the microwave energy pulse or a characteristic of an electrical transient, such as, for example, the duration of the first off period 210. A long "off" period may indicate that the target tissue contains excessive heat energy and the individual pulse parameter may be adjusted to deliver less energy. Alternatively, a short "off" period may indicate that the target tissue quickly disperses the heat energy in the target tissue and the energy of the first subsequent energy pulse should remain the same or may be increased.

Control of the first subsequent energy pulse 200a may be similar to the control of the initial energy pulse 200 or control may be responsive to a different measured parameter or different characteristic of an electrical transient. As the temperature "T" of tissue "PT" increases, steam begins to form at the molecular level and/or the tissue begins to transform. Steam generation and phase transformation effect thermal delivery and dispersion within the target volume and reflective power "RP" will begin to increase. At this point, parameters of the subsequent energy pulses 200c-200i are selected as to not appreciably heat the tissue "PT".

With continued reference to FIG. 4, reflective power "RP" may remain relatively constant during the initial delivery of electrosurgical energy, e.g. between 0 and about 45 seconds. As the temperature of the tissue increase, e.g. between about 45 seconds and about 60 seconds, the reflective power "RF" increases. When the reflective power "RP" exceeds a threshold value, the energy delivery may be decreased and/or the duration between energy subsequent energy pulses may be increased. The threshold value for reflective power "RP" may vary between about 1% and about 20% of reflective energy, typically about 5% of reflective energy.

A further embodiment of the present method includes the step of measuring at least one characteristic of the microwave energy pulse and determining whether to change the microwave energy parameters. The characteristic may be related to reflective power "RP", such as, for example, the instantaneous measurement or the rate of change of reflective power "ΔRP". Energy pulse parameters are selected as to control or maintain selected characteristics.

Reflective power "RP" and the rate of change of reflective power "ΔRP" can be used as an indicator of the condition of tissue. Formation of steam, while conducive to thermal delivery of heat, removes moisture from tissue and changes the impedance of the tissue. A change of tissue impedance creates an imbalance between the antenna and the tissue "PT" which causes an increase in reflective power "RP". In selecting parameters to maintain or reduce reflective power "RP", the system 10, while creating some steam, does not damage tissue "PT" resulting in more predictable and/or larger ablation sizes.

According to a further method of the present disclosure, at least one characteristic of the tissue "PT" is measured in response to the applied first pulse. The controller 22, in accordance with the measured characteristic may terminate the delivery of microwave energy to tissue. The controller 22 may also use the measured characteristic to determine a set of microwave energy parameters for a subsequent microwave energy pulse. The steps are then repeated for the subsequent pulses.

In a further embodiment of the present method, the set of microwave energy parameters for the subsequent microwave energy pulse includes a magnitude of a starting microwave power and a duration of the subsequent microwave energy pulse.

In a further method of the present disclosure, the delivery of electrosurgical energy, and/or the "off" period, may be adjusted for temperature management of portions of the electrosurgical system or temperature management of patient tissue "PT". With reference to FIG. 1, controller 22 of the electrosurgical generator 20 monitors at least one of the temperature of the transmission line 34 via line sensor 35 and/or the temperature of the device via device sensor 36. Device 20 may include one or more tissue temperature measuring sensors (not shown) or tissue measurement sensors may connect directly to electrosurgical generator. With reference to FIG. 4, energy delivery may be intermittently reduced or paused, or the "off" period may be increased, to allow the transmission line 34, device 20 or patient tissue "PT" to cool.

The system for supplying microwave energy for microwave therapy and the methods of use discussed above are not limited to microwave antennas used for hyperthermic, ablation, and coagulation treatments but may include any number of further microwave antenna applications. While several embodiments of the disclosure have been shown in the drawings and/or discussed herein, it is not intended that the disclosure be limited thereto, as it is intended that the disclosure be as broad in scope as the art will allow and that the specification be read likewise. Modification of the above-described system and methods for using the same, and variations of aspects of the disclosure that are obvious to those of skill in the art are intended to be within the scope of the claims. Therefore, the above description should not be construed as limiting, but merely as exemplifications of particular embodiments.

What is claimed is:

1. A system for supplying microwave energy to tissue, comprising:
   a housing;
   a microwave antenna having an elongated shaft configured for penetration into tissue, the elongated shaft extending from a distal end of the housing and configured to deliver microwave energy to tissue within a patient body;
   a transmission line cable electrically coupled to the microwave antenna and extending from a proximal end of the housing;
   a temperature sensor housed within the transmission line cable proximal to the housing; and
   an electrosurgical generator operatively coupled to the microwave antenna via the transmission line cable such that the temperature sensor is housed within the transmission line cable between the housing and the electrosurgical generator, the electrosurgical generator including:
      a microwave energy source; and
      a controller configured to cause the electrosurgical generator to deliver microwave energy to the elongated shaft of the microwave antenna, the controller determining a temperature of a portion of the transmission line cable between the housing and the microwave energy source as measured by the temperature sensor external to the patient body while the elongated shaft of the microwave antenna is positioned within the patient body and delivering the microwave energy to the tissue within the patient body.

2. The system according to claim 1, wherein the controller is configured to cause the electrosurgical generator to deliver two pulses of microwave energy through the microwave antenna.

3. The system according to claim 2, wherein the controller is configured to measure an electrical characteristic of at least one of the two pulses of microwave energy.

4. The system according to claim 3, wherein the controller is configured to determine a pulse parameter of a treatment microwave energy pulse based on the electrical characteristic of at least one of the two pulses of microwave energy.

5. The system according to claim 4, wherein the pulse parameter is selected from a group consisting of power, frequency, pulse duration, pulse duty cycle, and time between pulses.

6. The system according to claim 3, wherein the electrical characteristic of at least one of the two pulses of microwave energy is related to reflective power.

7. The system according to claim 3, wherein the electrosurgical generator further includes a user interface.

8. The system according to claim 7, wherein the controller is responsive to a user input from the user interface and configured to adjust a pulse parameter of the microwave energy based on the user input.

9. The system according to claim 1, wherein the electrosurgical generator further comprises a resistive load configured to absorb microwave energy supplied by the electrosurgical generator.

10. The system according to claim 9, wherein the controller is configured to cause the electrosurgical generator to switch delivery of microwave energy from tissue to the resistive load.

11. The system according to claim 1, further comprising a sensor disposed on the microwave antenna.

12. The system according to claim 11, wherein the sensor disposed on the microwave antenna is at least one of a temperature sensor or an impedance sensor.

13. The system according to claim 12, wherein the controller is configured to cause the electrosurgical generator to terminate delivery of microwave energy when a rate of change of tissue temperature exceeds a threshold value.

14. The system according to claim 1, wherein the transmission line cable includes a proximal end having a connector configured to connect to an output of the electrosurgical generator and a distal end configured to connect to the microwave antenna to electrically couple the microwave antenna to the electrosurgical generator.

15. The system according to claim 1, wherein the temperature sensor is enclosed within an outer surface of the transmission line cable.

16. The system according to claim 1, wherein the microwave antenna includes a tapered distal tip configured to penetrate tissue.

17. A system for supplying microwave energy to tissue, comprising:
   a housing;
   a microwave antenna having an elongated shaft configured for penetration into tissue, the elongated shaft extending from a distal end of the housing and configured to deliver microwave energy to tissue within a patient body;
   a transmission line cable electrically coupled to the microwave antenna and extending from a proximal end of the housing;
   a temperature sensor housed within the transmission line cable proximal to the housing; and
   a microwave generator coupled to the microwave antenna via the transmission line cable such that the temperature sensor is housed within the transmission line cable between the housing and the microwave generator, the microwave generator including a controller configured to cause the microwave generator to deliver microwave energy to the elongated shaft of the microwave antenna, the controller receiving a temperature signal from the temperature sensor to determine a temperature of a portion of the transmission line cable that is disposed between the housing and the microwave generator and external to the patient body while the elongated shaft of the microwave antenna is positioned within the patient body and delivering the microwave energy to the tissue within the patient body.

* * * * *